(12) United States Patent
Lambert et al.

(10) Patent No.: US 10,436,730 B2
(45) Date of Patent: Oct. 8, 2019

(54) SYSTEM AND METHOD FOR SENSING OIL QUALITY

(71) Applicant: Pitco Frialator, Inc., Bow, NH (US)

(72) Inventors: Nathaniel A. Lambert, Hookset, NH (US); Michael T. Fecteau, Derry, NH (US); Jason D. Finnie, Bow, NH (US); Jared C. Perkins, Chester, NH (US)

(73) Assignee: Pitco Frialator, Inc., Bow, NH (US)

( * ) Notice: Subject to any disclaimer, the term of this patent is extended or adjusted under 35 U.S.C. 154(b) by 336 days.

(21) Appl. No.: 15/379,052

(22) Filed: Dec. 14, 2016

(65) Prior Publication Data

US 2017/0176369 A1  Jun. 22, 2017

Related U.S. Application Data

(60) Provisional application No. 62/270,366, filed on Dec. 21, 2015.

(51) Int. Cl.
| | |
|---|---|
| *G01N 27/12* | (2006.01) |
| *G01N 33/03* | (2006.01) |
| *G01N 35/00* | (2006.01) |
| *G05D 7/06* | (2006.01) |
| *A47J 37/12* | (2006.01) |

(52) U.S. Cl.
CPC .......... *G01N 27/12* (2013.01); *A47J 37/1266* (2013.01); *G01N 33/03* (2013.01); *G01N 35/00584* (2013.01); *G05D 7/0617* (2013.01)

(58) Field of Classification Search
CPC ......... G01N 1/00; G01N 2201/00; G01R 1/00
USPC ........................................................ 324/693
See application file for complete search history.

(56) References Cited

U.S. PATENT DOCUMENTS

| | | |
|---|---|---|
| 4,148,729 A | 4/1979 | Howard |
| 4,210,123 A | 7/1980 | Moore et al. |
| 4,324,173 A | 4/1982 | Moore et al. |
| 4,487,691 A | 12/1984 | Panora |

(Continued)

FOREIGN PATENT DOCUMENTS

| | | |
|---|---|---|
| DE | 27 46 728 | 4/1979 |
| DE | 82 3 081.5 | 4/1990 |

(Continued)

OTHER PUBLICATIONS

International Search Report for PCT/US2016/061982, dated Jan. 31, 2017, 2 pp.

(Continued)

*Primary Examiner* — Jermele M Hollington
*Assistant Examiner* — Temilade S Rhodes-Vivour
(74) *Attorney, Agent, or Firm* — Brinks Gilson & Lione

(57) ABSTRACT

A system for measuring the state of degradation of cooking oil in a deep fryer is provided. The system includes a loop of piping fluidly connected to a fryer for selectively allowing flow of oil from the fryer and into the loop and for returning to the fryer. A pump urges the flow of cooking oil through the loop of piping and selectively to urge oil to return to the at least one fryer pot. The loop further comprises a return portion that extends from a discharge of the pump toward a suction of the pump. A sensor is disposed in the return portion of the loop and adapted to measure an electrical property that is indicative of total polar materials of said cooking oil. A vent line is provided in the return portion of the loop.

24 Claims, 7 Drawing Sheets

(56) References Cited

U.S. PATENT DOCUMENTS

| | | |
|---|---|---|
| 4,506,995 A | 3/1985 | Polster |
| 4,688,475 A | 8/1987 | Witt et al. |
| 4,742,455 A | 5/1988 | Schreyer |
| 4,764,258 A | 8/1988 | Kauffman |
| 4,908,676 A | 3/1990 | Bedell et al. |
| 4,959,144 A | 9/1990 | Bernard |
| 4,974,405 A | 12/1990 | Littau |
| 5,071,527 A | 12/1991 | Kauffman |
| 5,160,444 A | 11/1992 | McFarland |
| 5,179,891 A | 1/1993 | Chiu |
| 5,239,258 A | 8/1993 | Kauffman |
| 5,247,876 A | 9/1993 | Wilson et al. |
| 5,404,799 A | 4/1995 | Bivens |
| 5,523,692 A | 6/1996 | Kuroyanagi et al. |
| 5,594,327 A | 1/1997 | Sagredos et al. |
| 5,617,777 A | 4/1997 | Davis et al. |
| 5,776,530 A | 7/1998 | Davis et al. |
| 5,787,372 A | 7/1998 | Edwards et al. |
| 5,818,731 A | 10/1998 | Mittal et al. |
| 5,929,754 A | 7/1999 | Park et al. |
| 5,933,016 A | 8/1999 | Kauffman et al. |
| 5,942,269 A | 8/1999 | Casey et al. |
| 5,951,854 A | 9/1999 | Goldberg et al. |
| 5,954,933 A | 9/1999 | Ingalls et al. |
| 6,009,974 A | 1/2000 | Casey et al. |
| 6,127,185 A | 10/2000 | Melton et al. |
| 6,235,210 B1 | 5/2001 | Saksena |
| 6,274,850 B1 | 8/2001 | Mercer |
| 6,278,282 B1 | 8/2001 | Marszalek |
| 6,378,420 B1 | 4/2002 | Savage et al. |
| 6,436,713 B1 | 8/2002 | Onwumere et al. |
| 6,455,085 B1 | 9/2002 | Duta |
| 6,459,995 B1 | 10/2002 | Collister |
| 6,469,521 B1 | 10/2002 | Klun et al. |
| 6,553,812 B2 | 4/2003 | Park et al. |
| 6,600,306 B1 | 7/2003 | Pernot et al. |
| 6,602,533 B1 | 8/2003 | Smith et al. |
| 6,717,667 B2 | 4/2004 | Abraham et al. |
| 6,745,669 B2 | 6/2004 | Suzuki |
| 6,777,009 B1 | 8/2004 | Shealy |
| 6,783,685 B2 | 8/2004 | Hwang |
| 6,791,334 B2 | 9/2004 | Horie et al. |
| 6,822,461 B2 | 11/2004 | Klun |
| 6,873,916 B2 | 3/2005 | Kolosov et al. |
| 6,958,166 B2 | 10/2005 | Taylor |
| 7,019,654 B2 | 3/2006 | Danyluk et al. |
| 7,030,629 B1 | 4/2006 | Stahlmann et al. |
| 7,043,967 B2 | 5/2006 | Kauffman et al. |
| 7,043,969 B2 | 5/2006 | Matsiev et al. |
| 7,129,715 B2 | 10/2006 | Hayashi et al. |
| 7,132,079 B2 | 11/2006 | Onwumere et al. |
| 7,158,897 B2 | 1/2007 | Kolosov et al. |
| 7,210,332 B2 | 5/2007 | Kolosov et al. |
| 7,225,081 B2 | 5/2007 | Kolosov et al. |
| 7,239,155 B2 | 7/2007 | Byington et al. |
| 7,254,990 B2 | 8/2007 | Matsiev et al. |
| 7,287,431 B2 | 10/2007 | Liu et al. |
| 7,383,731 B2 | 6/2008 | Liu et al. |
| 7,390,666 B2 | 6/2008 | Onwumere et al. |
| 7,407,566 B2 | 8/2008 | Jiang et al. |
| 7,504,835 B2 | 3/2009 | Byington et al. |
| 7,504,836 B2 | 3/2009 | Chambon et al. |
| 7,521,945 B2 | 4/2009 | Hedges et al. |
| 7,523,006 B2 | 4/2009 | Muhl et al. |
| 7,523,646 B2 | 4/2009 | Klun |
| 7,600,424 B2 | 10/2009 | Sasaki et al. |
| 7,652,490 B2 | 1/2010 | Muhl et al. |
| 7,719,289 B2 | 5/2010 | Muhl et al. |
| 7,729,870 B2 | 6/2010 | Sun |
| 7,834,646 B2 | 11/2010 | Chambon et al. |
| 7,928,741 B2 | 4/2011 | Hedges et al. |
| 8,207,749 B2 | 6/2012 | Reime |
| 8,257,976 B2 | 9/2012 | Wei et al. |
| 8,287,182 B2 | 10/2012 | Muhl et al. |
| 8,325,345 B2 | 12/2012 | Mahmoodi et al. |
| 8,340,928 B2 | 12/2012 | Sun |
| 8,421,486 B2 | 4/2013 | Akiyama et al. |
| 8,432,171 B2 | 4/2013 | Coppe et al. |
| 8,436,629 B2 | 5/2013 | Chambon |
| 8,497,691 B2 | 7/2013 | Behle et al. |
| 8,505,443 B2 | 8/2013 | Abney et al. |
| 8,519,726 B2 | 8/2013 | Sun |
| 8,551,331 B2 | 10/2013 | Burkett et al. |
| 8,564,310 B2 | 10/2013 | Yu et al. |
| 8,614,588 B2 | 12/2013 | Hedges |
| 8,643,388 B2 | 2/2014 | Hedges |
| 8,689,679 B2 | 4/2014 | Tiszai et al. |
| 8,709,260 B2 | 4/2014 | Burkett et al. |
| 8,732,938 B2 | 5/2014 | Kolosov et al. |
| 8,736,282 B2 | 5/2014 | Chambon |
| 8,764,967 B2 | 7/2014 | Fan |
| 8,773,152 B2 | 7/2014 | Niemann et al. |
| 8,828,223 B2 | 9/2014 | Savage et al. |
| 8,829,928 B2 | 9/2014 | Gonzalez et al. |
| 8,847,120 B2 | 9/2014 | Burkett et al. |
| 8,854,058 B2 | 10/2014 | Katafuchi |
| 8,980,102 B2 | 3/2015 | Florkey et al. |
| 9,038,443 B1 | 5/2015 | Pace et al. |
| 9,161,659 B2 | 10/2015 | Lambert et al. |
| 9,170,144 B2 | 10/2015 | Qi |
| 9,176,086 B2 | 11/2015 | Qi |
| 9,228,965 B2 | 1/2016 | Burkett et al. |
| 9,261,659 B2 | 2/2016 | Shaw |
| 9,510,708 B2 | 12/2016 | Behle et al. |
| 2002/0035931 A1 | 3/2002 | Tschopp et al. |
| 2002/0046657 A1 | 4/2002 | Takahashi |
| 2002/0069767 A1 | 6/2002 | Wendel et al. |
| 2002/0082924 A1 | 6/2002 | Koether |
| 2004/0250622 A1 | 12/2004 | Kolosov et al. |
| 2005/0153022 A1 | 7/2005 | Schilling et al. |
| 2005/0247697 A1 | 11/2005 | Wu |
| 2006/0254432 A1 | 11/2006 | McLemore |
| 2007/0062515 A1* | 3/2007 | Mullaney, Jr. ...... A47J 37/1223 126/391.1 |
| 2007/0272209 A1 | 11/2007 | Matsiev et al. |
| 2008/0121578 A1 | 5/2008 | Burkett et al. |
| 2008/0196596 A1 | 8/2008 | Forrest et al. |
| 2008/0213446 A1 | 9/2008 | Feinberg et al. |
| 2008/0238445 A1 | 10/2008 | Muhl et al. |
| 2008/0282905 A1 | 11/2008 | Savage et al. |
| 2009/0044707 A1 | 2/2009 | Claesson et al. |
| 2009/0101023 A1* | 4/2009 | Kimura ............... A47J 37/1223 99/331 |
| 2009/0252842 A1 | 10/2009 | Wang et al. |
| 2009/0309619 A1* | 12/2009 | Behle ................. A47J 37/1223 324/698 |
| 2010/0000418 A1 | 1/2010 | Payen et al. |
| 2010/0201528 A1 | 8/2010 | Bruinsma et al. |
| 2010/0260903 A1 | 10/2010 | Wei et al. |
| 2011/0030486 A1 | 2/2011 | Hall et al. |
| 2011/0084708 A1 | 4/2011 | Yu |
| 2011/0234244 A1 | 9/2011 | Chambon |
| 2011/0238310 A1 | 9/2011 | Estrellado et al. |
| 2011/0267080 A1 | 11/2011 | Hedges |
| 2012/0022694 A1 | 1/2012 | Mohanty et al. |
| 2012/0062251 A1 | 3/2012 | Gonzalez et al. |
| 2012/0074125 A1 | 3/2012 | Burkett et al. |
| 2012/0075115 A1 | 3/2012 | Lee et al. |
| 2012/0229151 A1 | 9/2012 | Katafuchi |
| 2012/0229152 A1 | 9/2012 | Katafuchi |
| 2013/0036916 A1 | 2/2013 | Burkett et al. |
| 2013/0183421 A1* | 7/2013 | Evraets ................. B01D 29/09 426/417 |
| 2013/0214797 A1 | 8/2013 | Gruden |
| 2013/0278276 A1 | 10/2013 | Behle et al. |
| 2014/0130579 A1 | 3/2014 | Hedges |
| 2014/0130900 A1 | 5/2014 | Hedges |
| 2014/0188404 A1 | 7/2014 | Von Herzen et al. |
| 2014/0188407 A1 | 7/2014 | Von Herzen et al. |
| 2014/0266065 A1 | 9/2014 | Von Herzen et al. |
| 2015/0027205 A1 | 1/2015 | Brugger |

(56) References Cited

U.S. PATENT DOCUMENTS

| | | | |
|---|---|---|---|
| 2015/0272390 A1 | 10/2015 | Burns et al. | |
| 2015/0285777 A1* | 10/2015 | Baumann | G01N 27/24 73/64.56 |
| 2016/0033463 A1* | 2/2016 | Robertson | A47J 37/12 426/231 |

FOREIGN PATENT DOCUMENTS

| | | |
|---|---|---|
| DE | 298 12 263 U1 | 10/1998 |
| DE | 199 47 669 A1 | 5/2001 |
| DE | 100 53 250 A1 | 11/2002 |
| DE | 20 2005 007144 U1 | 7/2005 |
| DE | 10 2005 039480 A1 | 3/2007 |
| DE | 10 2006 003733 B3 | 3/2007 |
| EP | 0 561 583 A1 | 9/1993 |
| EP | 1 004 872 A1 | 5/2000 |
| JP | 2003 250708 A | 9/2003 |
| JP | 2005-055198 A | 3/2005 |
| WO | WO 02/04914 A2 | 1/2002 |
| WO | WO 2007/055980 A1 | 5/2007 |
| WO | WO 2009/005691 A1 | 8/2009 |
| WO | WO 2010/076839 A2 | 8/2010 |
| WO | WO 2012/012747 A2 | 1/2012 |
| WO | WO 2012/027304 A1 | 3/2012 |
| WO | WO 2012/031924 A1 | 3/2012 |
| WO | WO 2012/036964 A2 | 3/2012 |
| WO | WO 2013/036813 A1 | 3/2013 |
| WO | WO 2013/139354 A1 | 9/2013 |
| WO | WO 2014/167158 A1 | 10/2014 |
| WO | WO 2014/167159 A1 | 10/2014 |
| WO | WO 2014/181209 A1 | 11/2014 |
| WO | WO 2015/147886 A1 | 1/2015 |
| WO | WO 2015/090359 A1 | 6/2015 |
| WO | WO 2015/142283 A1 | 9/2015 |

OTHER PUBLICATIONS

Written Opinion for PCT/US2016/061982, dated Jan. 17, 2017, 8 pp.

Examination Report No. 1 for AU application No. 2016379162, dated Aug. 24, 2018, 3 pp.

International Search Report and Written Opinion for PCT/US2016/067179, dated May 12, 2017, 15 pp.

Deep Frying-Chemistry, Nutrition, and Practical Applications, $2^{nd}$ Edition, Michael D. Erickson, Editor, 19 pp.

Journal of Food Process Engineering, D.R. Heldman and R.P.Singh, CoEditora, Food & Nutrition Press, Inc., vol. 19, No. 2, Jun. 1996, 24 pp.

European Journal of Lipid Science and Technology, Official Journal of the European Federation for the Science and Technology of Lipids (Euro Fed Lipid), Special Topic: Deep Fat Frying-Healthier and Tastier Fried Food, Nov. 2004, www.ejlst.de, 9 pp.

Written Opinion of the International Searching Authority for PCT/US2015/037927, dated Oct. 8, 2015, 7 pp.

International Search Report for PCT/US2015/037927, dated Oct. 12, 2015, 4 pp.

English Translation of JP 2005-055198 submitted in IPR 2016-01435, 11 pp.

International Preliminary Report on Patentability for PCT/US2016/067179, dated Jun. 26, 2018, 8 pp.

Examination Report for EP application No. 16 837 995.6, dated Aug. 12, 2019, 4 pp.

* cited by examiner

SYSTEM AND METHOD FOR SENSING OIL QUALITY

CROSS-REFERENCE TO RELATED APPLICATIONS

This application claims priority from U.S. Provisional Application No. 62/270,366, filed on Dec. 21, 2015, the entirety of which is hereby fully incorporated by reference herein.

TECHNICAL FIELD

This disclosure relates to systems for measuring the quality of oil within a deep fat fryer system.

BRIEF SUMMARY

A first representative embodiment of the disclosure is provided. The embodiment includes a system for measuring the state of degradation of cooking oil in a deep fryer. The system includes at least one fryer pot and a loop of piping that is fluidly connected to said at least one fryer pot for selectively allowing a flow of oil from the at least one fryer pot into the loop and for selectively allowing the cooking oil to return to said at least one fryer pot from the loop. A pump is provided for urging the flow of cooking oil through the loop of piping and selectively to urge oil to return to the at least one fryer pot. The loop further comprises a first valve that is positionable to a closed position to prevent oil flow to or from the at least one fryer pot, and is positioned to an open position to allow flow to or from the at least one fryer pot. The loop further comprises a return portion that extends from a discharge of the pump toward a suction of the pump, wherein the return portion includes a second valve that is configured to selectively prevent or allow flow through the return portion. A sensor is disposed in fluid communication within the loop and adapted to measure an electrical property that is indicative of total polar materials of said cooking oil as the cooking oil flows within the loop of piping and past said sensor, the return portion of the loop additionally includes a vent line disposed proximate to the sensor, wherein fluid within the loop can flow into and through the vent line.

Another representative embodiment of the disclosure is provided. The embodiment includes a system for measuring the state of degradation of cooking oil in a deep fryer. The system includes at least one fryer pot and a loop of piping fluidly connected to said at least one fryer pot for selectively allowing flow of oil from the at least one fryer pot into the loop and for selectively allowing the cooking oil to return to said at least one fryer pot from the loop. A pump urges flow of cooking oil through the loop of piping and selectively to urge oil to return to the at least one fryer pot. The loop further comprises a first valve that is positionable to a closed position to prevent oil flow from the at least one fryer pot, and is positioned to an open position to allow flow from the at least one fryer pot. The loop further comprises a second valve that is positionable to a closed position to prevent oil flow to the at least one fryer pot, and is positioned to an open position to allow flow to the at least one fryer pot. The loop further comprises a recirculation portion that extends from a discharge of the pump toward a suction of the pump, wherein the recirculation portion includes a third valve that is configured to selectively prevent or allow flow through the recirculation portion. A sensor is disposed in fluid communication within the loop and adapted to measure an electrical property that is indicative of the quality of the cooking oil within the loop of piping, wherein the sensor is disposed in the recirculation portion of the loop. During cooking operations within the fryer pot the first and second valves are in the closed position, and during an operation of the sensor the first and second valves are shut. The recirculation portion includes a vent line that is disposed for fluid communication proximate to the sensor to drain cooking oil from the recirculation portion.

Yet another representative embodiment is provided. The embodiment includes a system for measuring the state of degradation of cooking oil. The system includes a vat for receipt of cooking oil, the vat remote from a device used to cook food product with cooking oil. A pump is in fluid communication with the vat, the pump fluidly connected to take suction from the vat. A sensor is disposed in fluid communication within the vat and adapted to measure an electrical property that is indicative of the quality of the cooking oil within the vat. The sensor is disposed in a fluid conduit that is in fluid communication with the pump, further comprising a vent line disposed in fluid communication with the fluid conduit proximate to the sensor, the vent line in communication with the vat.

Yet another representative embodiment is provided. The embodiment includes a system for measuring the state of degradation of cooking oil in a deep fryer. The system includes at least one fryer pot and a loop of piping is fluidly connected to said at least one fryer pot for selectively allowing flow of oil from the at least one fryer pot into the loop and for selectively allowing the cooking oil to return to said at least one fryer pot from the loop. A pump is provided for urging the flow of cooking oil through the loop of piping and selectively to urge oil to return to the at least one fryer pot. The loop further comprises a recirculation portion that extends from a discharge of the pump toward a suction of the pump, wherein the recirculation portion includes a first valve that is configured to selectively prevent or allow flow through the recirculation portion. A sensor is disposed in fluid communication within the loop and adapted to measure an electrical property that is indicative of the quality of the cooking oil within the loop of piping, wherein the sensor is disposed in the recirculation portion of the loop. A vent line is positioned within the recirculation portion and proximate to the sensor.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Figure 1:
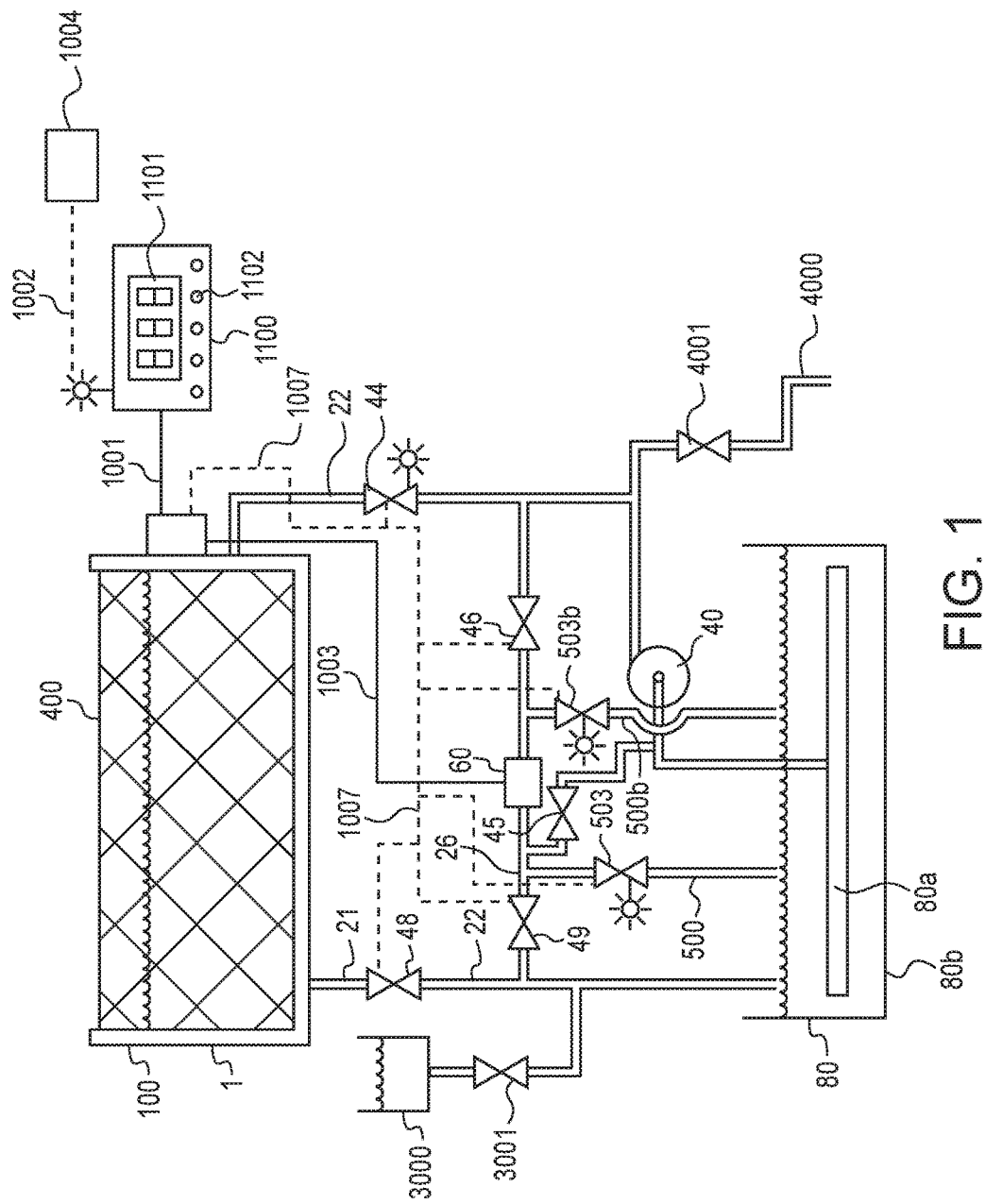
FIG. 1 is a schematic of a loop for oil from a deep fat fryer depicting a recirculation line within the loop and vent lines in two potential locations disposed in fluid communication with the recirculation line.
Figure 2:
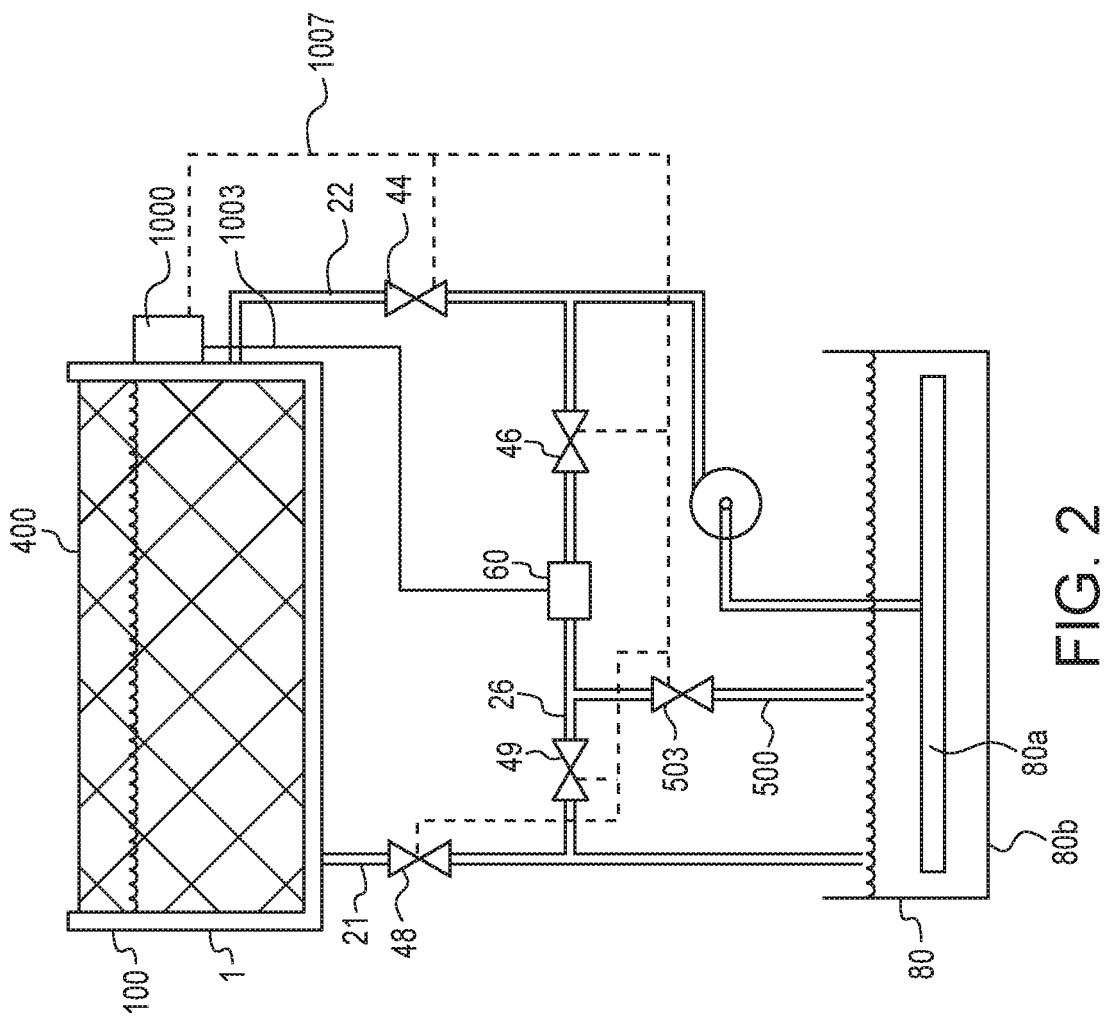
FIG. 2 is a simplified version of the loop of FIG. 1 schematically depicting the valves in the loop communicating with a controller.

Turning now to FIGS. 1-4, a system 10 for sensing the quality of oil in a deep fat fryer 1 is provided. The system 10 may be fluidly connected to a deep fat fryer 1, such that the system 10 can be either by continuously, cyclically, or manually used to measure the quality of oil located in the vat of the fryer, and can be operated during cooking operations of the fryer 10 or when cooking operations are not occurring in the fryer 10.

The system 10 may be fluidly connected to at least one fryer pot (frypot) 100, which is configured to hold a volume of oil, which is normally heated by one or more conventional electric heaters or gas burners which are in thermal communication with the frypot 100. The frypot 100 may be configured to receive one or more baskets 400 that are used to place food product within the heated oil to fry the food. With continued use, the oil within the frypot tends to become degraded through prolonged interaction with the food product as well as due to other factors, such as oxidation, hydrolysis, etc.

The frypot 100 may be fluidly connected to the system 10 with one or more oil outlets 21, and in some embodiments with one or more oil inlets 22. The system 10 may include a filtration system 80, a pump 40, a recirculation system 26, and an oil sensor 60, each discussed below. The system 10 may be formed as a loop 20 piping (such as rigid or flexible piping, or other types of conduit), that is configured to selectively allow the flow of oil from the at least one frypot 100, through the loop, and ultimately return to the at least one frypot 100 (FIG. 1). The system 10 may include a drain 4000, which may be controlled by a valve 4001 for selectively opening and closing the drain 4000. The valve 4001 may be a manual valve, or in some embodiments, the valve 4001 may be a remotely operated valve, such as a solenoid valve, and may be operable by a controller 1000. As discussed elsewhere herein, the controller 1000 may operate the drain valve 4001 for several reasons, such as to dump oil from the system 10 (and therefore the frypot 100), to "feed and bleed" oil (i.e. simultaneous dumping of oil from the drain 4000 and replacement with fresh oil from the storage vat 3000 (by operating the replacement valve 3001)). As discussed elsewhere herein, the controller 1000 may be programmed to automatically dump or feed and bleed oil from the system due to the measured quality of the oil by the sensor 60.

In some embodiments, the one or more oil outlets 21 from the frypot 100 may be selectively isolated by a valve 48 (or valves 48) that may be manual valves or remotely operable valves, such as solenoid valves. Similarly, the one or more oil inlets 22 to the frypot 100 may be selectively isolated by a valve 44 (or valves 44) that may be manual valves or remotely operable valves, such as solenoid valves.

The sensor 60 may be an electrical sensor that is adapted to continuously measure one or more electrical parameters of the oil which are directly indicative, or representative of the amount of impurities in the oil flowing through/past the sensor 60. For example, it is a well-known attribute of cooking oil to measure the total polar materials, or total polar compounds, therewithin and it is known that the amount of total polar materials/compounds increases as the life of the cooking oil decreases (i.e. the amount of total polar materials/compounds increases as the oil is used for longer time periods). The sensor 60 may be configured to continuously measure the capacitance of the oil flowing past/through the sensor, which is representative of the total polar materials/compounds in the oil, due to the known proportionality between the total polar materials/compounds in the oil and the dielectric constant of the oil. Still further, the sensor may be configured to measure voltage, resistance, dielectric, conductivity, or conductance of the oil, some or all of which may be indicative of total polar materials or other aspects of oil that relate to the overall quality of the oil, and in some embodiments, the sensor may be configured to measure more than one (or all) of these parameters.

The oil sensor may be a coaxial sensor, or a resonant sensor, or another type of sensor known in the art to be capable of sensing one or more electrical parameters of oil (such as those listed above) in order for the sensor to determine the total polar compounds/materials within the oil to allow for an oil quality determination to be made, such as by the controller 1000.

The sensor 60 may provide a signal 1003 to the controller 1000 that is indicative of the measured electrical property of the oil. In some embodiments, the controller 1000 may receive the signal 1003 and perform one or more of the functions discussed herein. For example, the controller 1000 may compare the measured electrical property of the oil to a programmed value (or range) of the electrical property. If the controller 1000 detects that the measured property is satisfactory (such as it is above or below a setpoint, or it is within a programed acceptable range), the controller may provide an indication to the user that the oil quality is acceptable, such as through a readout 1101 on a display 1100 associated with the fryer, or on a remote device 1004 that communicates remotely 1002 (as schematically depicted in FIG. 1) with the controller 1000 (or display 1100), such as through Wi-Fi, Bluetooth or another available remote communication means 1110.

In some embodiments, and as shown in FIG. 1, the sensor 60 may send an output signal 1120 directly to the display 1100.

In some embodiments where the sensor 60 may be multiple sensors that can simultaneously or non-simultaneously measure multiple different properties of oil, the user may control which property is sensed (or displayed) and the controller or the display may communicate with the sensor 60 to control the operation of the sensor, or otherwise direct the monitoring of the sensor. If the fryer is configured with an automated filtration system, the controller 1000 may send a signal to the automated filtration system that further filtration, or a batch filtration if the system is adapted for continuous filtration of a portion of the oil within the system, is unnecessary.

If the controller 1000 determines that the measured property is unsatisfactory (such as above a setpoint or within a range indicative of poor oil quality) the controller may provide an alarm to the user. The controller may also send a signal to an automated filtering system (when provided) indicating that a batch filter cycle is recommended (or perhaps required, such as immediately or after a current cooking cycle is completed). Further the controller 1000 could initiate an auto top-off system (when provided with the fryer) to automatically provide new oil to the frypot 100 and simultaneously open the drain valve 4001 to "feed and bleed" the poor quality oil with new oil, and potentially without interrupting cooking operations within the frypot. Moreover, if the measured property is above a setpoint, below a setpoint, or outside of an acceptable range, the controller could turn off the fryer (potentially when an in-process cooking cycle is completed) and cause an automatic draining (and disposal) of the frypot 100 and an automated refill of oil within the frypot (when an auto top-off system is provided), or automatically drain, and dispose of the oil and signal to the user that the frypot must be manually refilled.

The sensor 60 may be arranged to extend inline within the flow of oil through the system 10. In some embodiments, the sensor 60 may be disposed within a recirculation line 26 of the system 10, which is a line that extends generally between the discharge 42 of the pump 40 and the filter vat 80b, and allows for oil to flow through the filtration system 80 and the pump without returning to the fryer pot 100. In some embodiments, the recirculation line 26 may include isolation valves 46, 49 on opposite sides of the sensor 60 (which may be manually or automatically controlled, such as by the controller 1000) such that the system 10 may be configured to isolate the sensor 60 and prevent oil flow therethrough, or configured to allow flow through the sensor 60. As discussed herein, the valves 44, 48 that selectively isolate the inlet and outlet 22, 21 of the frypot, respectively, may be controlled in conjunction with the operation of the sensor 60 within the recirculation system. For example, when the sensor 60 is operated in the recirculation system, the valves 44, 48 may be shut so that the pump 40 urges oil flow only through the recirculation system and the sensor 60 and the filter vat 80 (with the valve positions schematically depicted in the figures, e.g. "O" for open, "S" for shut). This configuration might be useful to monitor the reduction of the capacitance (or the change in any other electrical characteristic discussed herein or otherwise known), and therefore total polar materials/compounds or any other electrical property of the oil monitored by the sensor 60 (discussed above), which could provide an indication of the operability or effectiveness of the filter 80 over time with continued flow.

Alternatively, in other embodiments, the sensor 60 may be operated with the valves 44 and 48 open (and with the recirculation line isolation valves 46, 49 open which allows for the oil from the frypot to be filtered continuously, as schematically depicted in FIG. 1, with the possible valve positions, "O" for open, "C" for closed) and the portion of the oil discharged from the pump 40 that runs through the recirculation line 26 (instead of returning to the frypot 100) measured. This type of operation would allow for continuous filtration and monitoring, if desired.

In some embodiments, the sensor 60 may be operated with the isolation valves 46, 49 shut, such that the sensor 60 would measure the electrical characteristic of the slug of oil disposed proximate to the sensor between the valves 46, 49. This configuration may be appropriate for sensors that more accurately measure an electrical characteristic of oil that is cooled significantly below normal cooking temperature of the oil. In some embodiments, the sensor 60 may be configured to measure the electrical characteristic of the oil that is either flowing past the sensor or relatively still (i.e. when the isolation valves 46, 49 are shut).

In some embodiments and as shown in FIG. 1, in some embodiments, the loop may include a pipe 27 that extends from downstream of the sensor 60, but before the downstream isolation valve 49 directly to the suction of the pump 40 (or alternatively downstream of the downstream isolation valve 49), therefore allowing flow through the sensor 60 that bypasses the filtration system 80. In some embodiments the pipe 27 may be selectively isolated by a valve 45.

In some embodiments, the loop may include one or more vent lines 500 that allow for cooking oil within the loop 20 to gravity drain from the loop 20. One or more vent lines 500 may be provided to allow for cooking oil that is within the loop that is still or stagnant to drain from the loop rather than remaining in place, which could lead to various problems. For example, when the system uses cooking oil that comprises solid shortening, the cooking oil is viscous when at an increased temperature, but becomes solid as the temperature of the cooking oil approaches normal ambient temperature within a commercial kitchen. The existence of the vent line 500 which allows stagnant hot cooking oil to drain from the loop (such as for example to the filter vat 80b (when provided) or to an external container prevents the possibility that the cooking oil would become solid within the loop, which may impede future flow through the loop either temporarily or permanently. The vent line 500, and specifically when the isolation valve 503 in the vent line 500 (when provided) is open, may also prevent flow blockage due to vapor locks or other fluid phenomena associated with fluid systems by opening the recirculation line 26 to the ambient. Finally, in some embodiments, the sensor 60 may be rendered inoperable, or loose calibration, when the sensor is in constant presence of oil, and the existence of the vent line 500 allows oil proximate to the sensor 60 to drain from the loop when the sensor is not in use to avoid these possible problems.

As depicted in FIG. 1, the vent line 500 may be positioned within the recirculation line 26, and in some embodiments proximate to the sensor 60. In some embodiments, the vent line (depicted in this position as 500b) may be between the upstream recirculation line isolation valve 46 (when provided) and the sensor 60, while in other embodiments, the vent line 500 may be between the downstream recirculation line isolation valve 49 (when provided) and the sensor 60 (depicted as vent line 500). In some embodiments, vent lines 500 may be provided in both locations. In embodiments, where the piping that forms the recirculation line 26 is not horizontal, the vent line 500 may be positioned at the pipe, and in some embodiments at the bottom of the pipe, that has the lowest position, so that oil from within the entire recirculation line is urged to the vent line 500 by gravity.

The vent line 500 may include an isolation valve 503 can be closed to prevent flow through the vent line 500 and opened to allow flow through the vent line 500. In some embodiments, the isolation valve 503 is positioned as close as possible to the recirculation piping 26 to minimize the volume within the vent line 500 that is between the recirculation line 26 and the isolation valve 503. The isolation valve 503 may be manually controlled, and/or may be automatically and remotely controlled by the controller 1000. When discussing that the controller 1000 controls the valve position of the isolation valve 503, one of ordinary skill in the art will understand that the controller 1000 may provide a signal to the isolation valve 503 that urges the valve to change position, either by energizing a motor that changes position of the valve, or through a linear actuator to change valve position, or through a solenoid controller for the isolation valve.

In some embodiments, the isolation valve 503 may be controlled by the controller 1000 such that the vent line 500 is open (with the isolation valve 503 opened) when one or both of the recirculation line isolation valves 46, 49 are shut, which allows the cooking oil within the recirculation line 26 to drain from the recirculation line. In embodiments where a pipe 27 is provided between the sensor 60 and the suction of the pump 40, the vent line valve 503 may be open when the isolation valve 45 of the pipe 27 is shut. In some embodiments, the controller 1000 may operate the vent line valve 503 to be in an opposite position from the return line 22 isolation valve 44. The possible valve positions of these valves as operated by the controller 1000 (the controller signal shown schematically as 1007) are in FIGS. 2 and 3.

Figure 3:
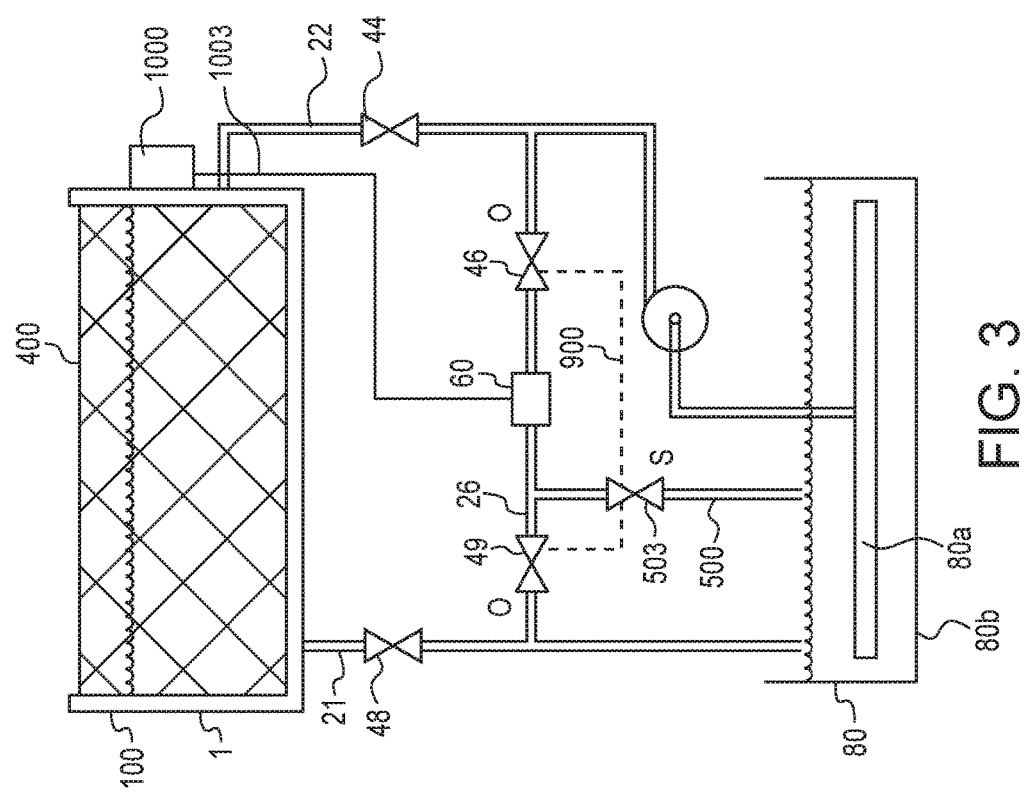
FIG. 3 is a simplified version of the loop of FIG. 1 schematically depicting the recirculation line isolation valves communicating with the vent line isolation valve.
Figure 4:
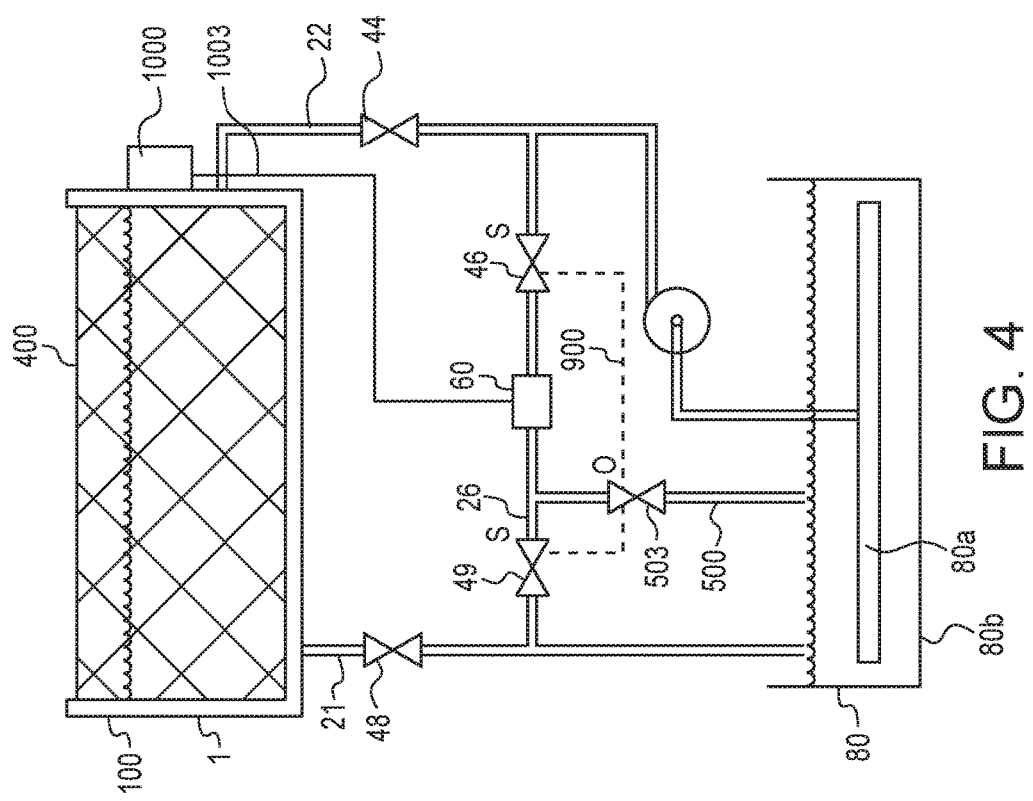
FIG. 4 is the view of FIG. 3 with the vent line isolation valve open when the recirculation line isolation valves are shut.

In other embodiments and as show schematically in FIGS. 3-4, the position of the vent line isolation valve 503 may be controlled via a master/slave relationship with the position of another valve (or valves) of the loop. For example, the vent line isolation valve 503 may be controlled to have an opposite position as the upstream recirculation line isolation valve 46, e.g. when valve 46 is open, the vent line isolation valve is shut (FIG. 3), and vice versa (FIG. 4). Alternatively, the vent line isolation valve 503 may be controlled to have the opposite position to the downstream recirculation line isolation valve 49. Alternatively, the vent line isolation valve may have a master/slave relationship with another valve in the system. The master/slave system works by the master valve sending a valve position signal 900 (either representative of the master's valve position, or through logic the opposite position that is desired for the slave vent line isolation valve 503, as appropriate) which causes the vent line isolation valve 503 to be repositioned (with a motor, linear actuator, solenoid, etc.). One of ordinary skill in the art with a thorough review of this specification will understand that the position of the vent line isolation valve 503 may be controlled (either by a controller, through a master/slave system, or manually by the operator) to allow for the oil line to be vented when the sensor is not desired to sense oil quality, and that the system may be set up in various was that would be understood by one of ordinary skill to achieve these goals without undue experimentation.

In some embodiments, the vent line may have an internal diameter that is smaller than an internal diameter of the piping that forms the loop, and specifically the piping that forms the recirculation line 26. For example, in some embodiments, the vent line 500 may have an internal diameter that is 3 times smaller than an internal diameter of the recirculation line 26 piping. In other embodiments, the vent line may have an internal diameter that is 2, 4, 5, 6, 7, 8, 9, or 10 times smaller (as well as all ratios between these whole number ratios that are possible with conventional English (feet/inches) or metric (cm/mm) piping sizes. Because the flow of cooking oil through the vent line 500 may often yield the benefits of providing a vent line discussed above, relatively small vent lines when compared to the size of the recirculation line piping may be preferred, such as to minimize oil flow through the vent line 500 if, for example, the vent line isolation valve 503 failed open.

Figure 5:
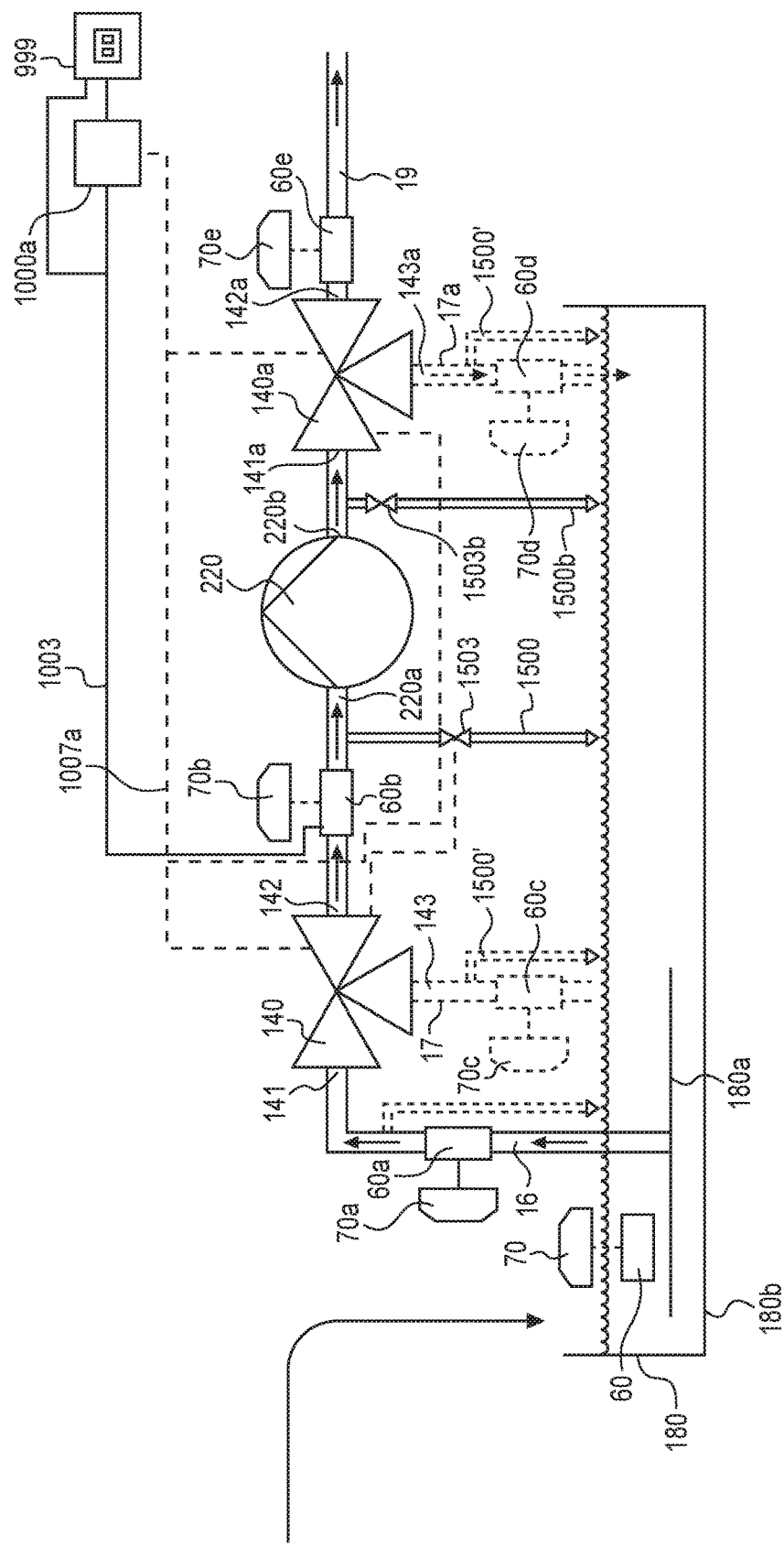
FIG. 5 is a schematic view of an oil filtering system depicting an oil sensing system in several potential positions within the oil filtering systems, with a vent line in multiple potential positions.
Figure 6:
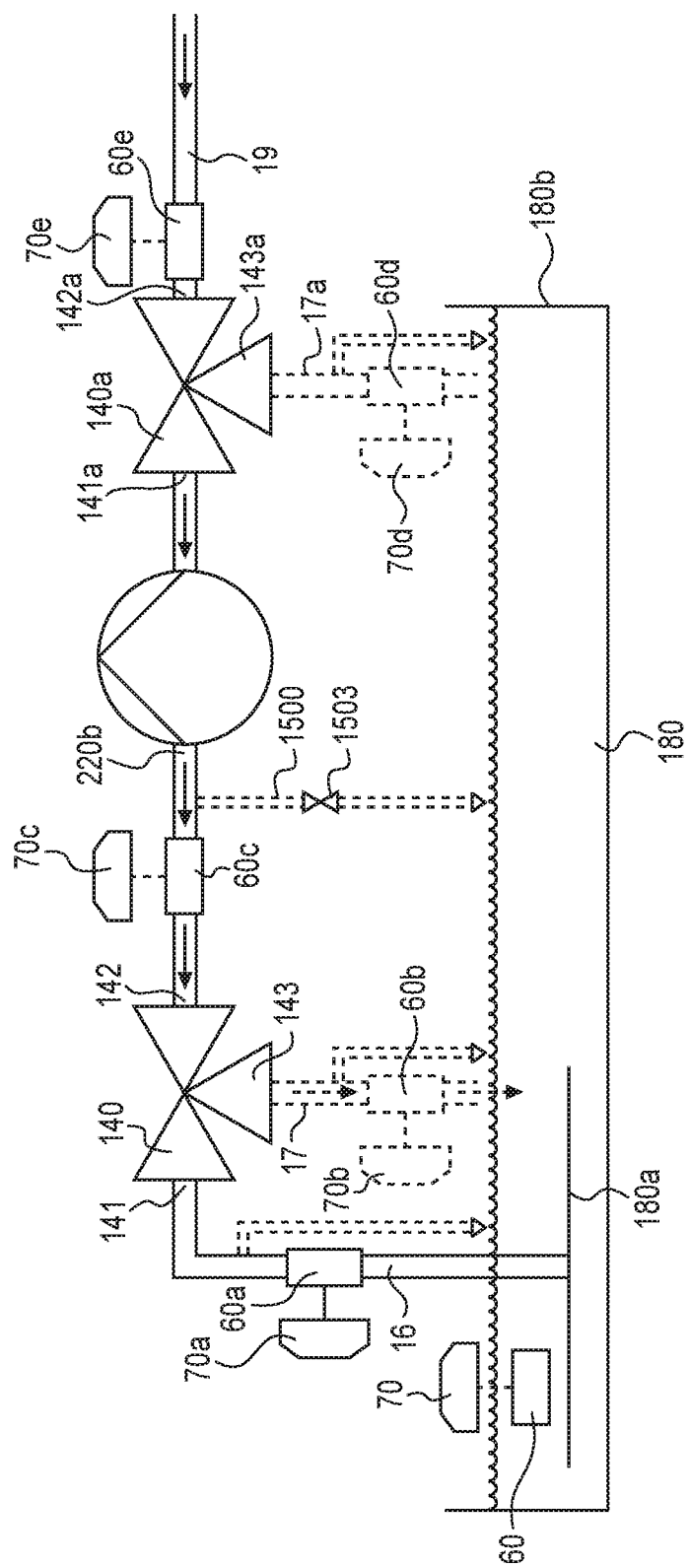
FIG. 6 is a simplified schematic of the view of FIG. 5, wherein the system is aligned to pump oil toward the vat.
Figure 7:
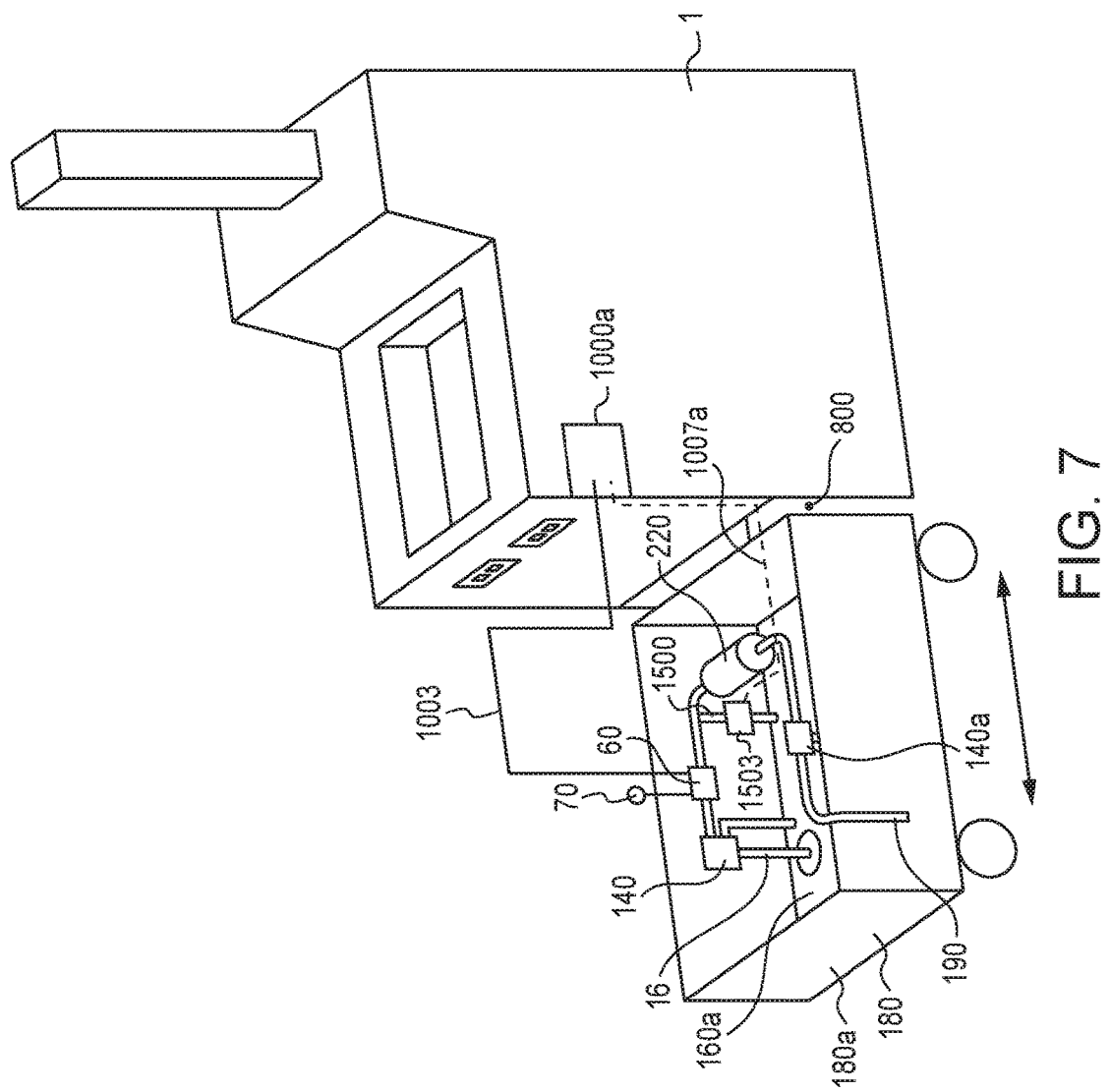
FIG. 7 is a schematic view of a fryer with the oil sensing system of FIG. 5.

Turning now to FIGS. 5-7, a system 180 for sensing the quality of oil that is associated with a cooking appliance 1 is provided. The system 180 may be fluidly connected to a cooking appliance, such as deep fat fryer 1, such that the system 180 can be either be continuously, cyclically, or manually used to measure the quality of oil that is representative of the oil located in the cooking device.

In some embodiments, the system 180 may be associated with a filtering system for a cooking appliance, such as a portable filtering system 180, as shown schematically in the figures. The portable system may include a vat 180*b* for receiving and holding cooking oil with a receiving space and that supports a filter material 180*a*. The filter material 180*a* is configured to remove foreign matter, crumbs and/or other impurities from the oil disposed within the vat that passes through the filter material. The filter material 180*a* may be a conventional filter for cooking oil, such as with one or more of a filter screen, a mesh, a paper, or a fabric that is used to mechanically and/or chemically remove particles and impurities from oil (due to oxidation or hydrolysis, for example) within the vat 180*b*, and specifically as oil passes through the filtering material.

The vat 180*b* of the portable filter system 180 may receive oil that is drained from the cooking appliance, such as a deep fat fryer 1, and specifically from the container that holds the oil within the cooking device, such as a frypot 1. The vat 180*a* may be configured to receive cooking oil from a plurality of different cooking appliances that are used in the same facility, such as a bay of frypots used within a bank of deep fat fryers.

The vat may be rigidly fixed to a cooking appliance 1, such as within the housing in a space 800 below a frypot 1 (FIG. 7) and equipment used to heat the oil within the frypot 100, such as a gas burner system (not shown). In some embodiments, the vat 180*b* may be slidably or rollably mounted upon the housing of the cooking appliance such that the vat is normally disposed within or directly below the housing, such as during cooking operations of the cooking appliance, and may be slid out of at least a portion of the housing to allow for easy access to the components of device 10.

The vat 180*b* may support a pump 220 that is fluidly connected to the vat 180*b*, and specifically to a volume of oil that is disposed within the vat 180*b*. In some embodiments, a suction 140*a* of the pump (FIG. 1) is fluidly connected with the vat such as to take suction from the vat, and a discharge 220*b* of the pump 220 extends away from the vat 180*b*, such as to direct oil to exit the system and, if aligned with respect to a cooking device, to return the cooking oil to the cooking device, such as the frypot of a deep fat fryer. As shown schematically in FIG. 7, the discharge 220*b* of the pump may be fluidly connected to a return hose or pipe 190.

In some embodiments, device may be configured such that the discharge 220*b* of the pump 220 is aligned to direct oil to a disposal container, or to another frypot, different from the frypot from which the oil in the vat 180*b* was received. In some embodiments shown in FIG. 6, the pump 220 may be operable in the opposite direction, such that the pump discharge 220*b* is fluidly connected (assuming that the valve 140*a* is aligned for flow from the second port 142*a* to the first port 141*a*) such that oil is pumped to the vat 180*b*. Other than this reverse direction of flow (and the changes necessary to accommodate this change of flow that would be understood by one of ordinary skill with reference to this specification), the system of FIG. 6 may be constructed and operated in the same as the system of FIG. 5 discussed herein. One of ordinary skill in the art, with a thorough review of this specification and drawings, will understand that the device 180 can be aligned (with differing pumping directions and valve positions, discussed herein) for flow in various directions and sensing oil quality with various sensors 60, 60*a*, etc. for different operational needs in conjunction with filtering. The sensors 60, 60*a* etc. may be the same as the sensor 60 discussed with the embodiments above.

In some embodiments, one or more valves 140 (140*a*) may be provided that is disposed with respect to the pump 220 and the vat 180*b*. In some embodiments, the valve 140 may be positioned upstream of the pump 220, such that the valve 140 is fluidly connected to the suction 220*a* of the pump 220, while in other embodiments, the valve may be positioned (as shown as 140*a* in FIG. 5) such that it is fluidly connected to the discharge 220*b* of the pump 220. In some embodiments, the valve 140*a* may be provided instead of valve 140, while in other embodiments, both valve 140 and valve 140*a* may be provided on opposite sides of the pump 220. In some embodiments, the valve 140 (140*a*) may be a valve with a single inlet and a single outlet.

In some embodiments, the valve 140 may be a three way valve that can be selectively aligned for the desired flow through the system 10. For example, the valve 140 may have a first port 141 that is fluidly connected to a pick up tube 16, which is fluidly connected to the vat 180*b*, and specifically the pickup tube 16 may be fluidly connected to the filter 180*a* such that oil that flows through the pickup tube 16 has passed through the filter 180*a*. The valve 140 may have a second port 142 that is fluidly connected to the suction 220*a* of the pump 220. The valve 140 may have a third port 143 that is fluidly connected to a return 17 that directs oil to the vat 180*b*. In some embodiments, the valve 140 (140*a*) is aligned such that flow from the first port 140*a* is directed to one of the second and third ports 140*b*, 140*c*, but not to both ports simultaneously. In other embodiments, the valve 140 (140*a*) may be aligned such that a portion of the cooking oil that flows into the valve through the first port flows through each of the second and third ports 140*b*, 140*c*.

In embodiments when the valve 140*a* is provided, the valve 140*a* may be a three way valve and be constructed in a similar manner as the valve 140 discussed above, although the various ports of the valve 140*a* are connected to different components of the system 10. For example, the valve 140*a* may have a first port 141*a* that is fluidly connected to the discharge 220*b* of the pump 220, a second port 142*a* that is fluidly connected to return piping 19 (discussed elsewhere herein), and a third port 143*a* that is fluidly connected to a return 17*a* that directs oil to the vat 180*b*.

One or both of the valves 140, 140*a* may be manually operated to allow the valve to be aligned for flow in the desired direction, such as from the first port 141 to the second port 142, or from the first port 141 to the third port 143. In some embodiments, one or both of the three way valves 140, 140*a* may be automatically operable, such as via an automatic operator associated with the valve to allow for the operator to control the position of the valve (either remotely or at the valve) but without the user needing to physically reposition the valve. In some embodiments a controller 1000*a* (similar to controller 1000 and shown schematically in FIG. 5 may be provided that sends a signal 1007*a* to the valve 140 (140*a*) to be repositioned, either based upon instructions from the user or automatically generated by the controller 1000.

A vent line 1500 may be fluid connected to the piping that is disposed between the valves 140 and 140*a*, which may drain to the vat 180*b*. The vent line 1500 may be similar in construction and operation to the vent line 500 discussed above (including the placement with respect to the sensor discussed above as well as the potential relative sizes of the vent line with respect to the piping that the vent line 1500 connects to. The vent line 1500 may include an isolation valve 1503 that may be similar in construction to the isolation valve 503 discussed above, while in other embodiments the vent line 1500 may not include an isolation valve and therefore may be constantly open to the atmosphere (or directed within a pool of oil if the oil depending upon the volume of oil in the filter vat 180*a*).

Specifically, the valve 1503 may be a manual valve and/or may be an automatically controlled valve, that is controlled either by a controller, or based upon the valve position of another valve, such as one of valves 140, 140*a* in a master/slave relationship, with the valve position of the respective valve 140, 140*a* causing a signal to be sent to the isolation valve 1503 to control its valve position. For example, the isolation valve 1503 may be configured to be open when one or both of the valves 140, 140*a* are shut, and the isolation valve 1503 may be shut when one or both of the valves 140, 140*a* are open. A signal (shown schematically in FIG. 5 as 900) may be sent between valves 140/140*a* and valve 1503 to coordinate this master/slave relationship, or the relationship may be controlled by the controller 1000*a*. In embodiments where the valve 140 is a three way valve, the isolation valve 1503 may be controlled to the open position when the valve 140 is ported to allow flow between ports 141 and 143, as discussed above, and/or the isolation valve 1503 may be open when the second valve 140*a* is ported from ports 141*a* to 142*a*.

One of ordinary skill in the art upon a thorough review of this specification will understand that the vent line 1500 is provided for similar reasons as the vent line 500 being provided in the embodiments discussed above, specifically to prevent a slug stagnant cooking oil remaining in the system, and potentially proximate to the sensor 60 (depending upon the sensor position 60*a*, 60*b*, etc. chosen for the system). One of ordinary skill in the art will understand the appropriate position of the vent isolation valve 1503 (as well as the proper system and operation to control the vent line isolation valve 1503 depending upon the remaining operational parameters of the system 2000 with the intended functionality of the vent line 1500 with respect to the system 2000 in mind, without undue experimentation.

As depicted in FIG. 5, a vent line (depicted as vent line 1500) may be disposed between the valve 140 and the suction of the pump (either upstream or downstream of the sensor 60*b*), and/or a vent line may be positioned downstream of the discharge of the pump 220 (depicted as vent line 1500*b*). Vent lines 1500 can be positioned at other locations within the system 180 that would be understood one of ordinary skill in the art, after a thorough review of this disclosure, to satisfy the purpose of providing the vent line 1500 as discussed herein. Several of these potential other locations for vent lines (depicted as 1500' in the figures) are depicted in FIGS. 5 and 6, and only one vent line may be provided or two or more vent lines may be provided. The vent lines 1500 may or may not include an isolation valve.

One or more sensors 60 may be provided at one or more locations within the device that receives oil during operation of the system. The sensor 60 may be provided at a location that is in fluid communication with the vat 180*b*, such that the sensor measures a parameter (discussed above) of the oil within the vat 180*b* (or after passing through the filter 180*a*. Because the device 1 is configured to filter oil that is received from a cooking device, such as a deep fat fryer, and upon filtering the oil return the newly filtered oil to the cooking device, the parameter of the oil measured by the sensor 60 is representative of the quality of the oil that eventually would be returned to the cooking device for use with cooking a food product.

As discussed above, the sensor 60 may be provided in many different positions within the device. FIGS. 5 and 6 depict the sensor 60 in multiple different positions within the device. One of the possible locations for the sensor is identified with the element number 60, while other potential locations for the sensor are depicted with the element number 60 and a corresponding letter, such as 60a, 60b, etc. The specific locations of for sensors that are depicted in the figures are disclosed herein. It is contemplated that the device may include only one sensor, which may be at any desired location of the possible locations discussed herein and depicted in the figures, or in some embodiments, more than one sensor (at two or more of the locations) may be provided within the device. Unless described herein to the contrary, each sensor depicted in the figures and described herein shall be the same in structure and operation as the sensor 60 described below.

The sensor 60 may include an antenna 70 that is configured to send a signal that is proportional to the parameter(s) of the oil measured by the sensor 60 to a display (not shown) or to the controller 1000a. The controller 1000a may reside on the system 180 or may be a part of the cooking appliance. The antenna 70 may be configured to pass a wireless signal (such as through Wi-Fi, Bluetooth, or other wireless transmission systems) and/or may pass a signal via a wired interface. As with the sensors, the antenna 70 may be provided with the sensor regardless of the position of the sensor 60 within the device, and for the sake of clarity, each sensor in different possible positions (e.g. 60a, 60b, etc.) is drawn with a corresponding antenna with the same reference character (e.g. 70a, 70b, etc.). As with the sensors 60, 60a, etc., the antennas, regardless of position, may operate in the same manner as the antenna 70 discussed above.

As mentioned above, the sensor 60 (and antenna 70 when provided) can be provided in numerous different positions with respect to the device 10. For example, the sensor 60 may be provided to interact with oil that rests within the vat 180b. Alternatively or additionally, the sensor 60a may be provided to interact with oil that flows through the take up pipe 16 that receives oil that has passed through the filter 14 and prior to the oil reaching the first valve 40 (when provided), or prior to reaching the suction 20a of the pump. Still alternatively or additionally, the senor 60b may be provided between the first valve 40 and the suction 20a of the pump.

Still alternatively or additionally, the sensor 60c may be provided in fluid communication with the third port 43 of the first valve 40 such that the oil that interacts with the sensor 60c is directed to return to the vat 12. Alternatively or additionally, the sensor 60d may be provided in fluid communication with the third port 43a of the second valve 140a, such that oil that interacts with the sensor 60d is directed to return to the vat 180b. Finally, alternatively or additionally, the sensor 60e may be provided proximate to the second port 142a of the second valve (when provided, or alternatively downstream of the discharge 220b of the pump 220), such that the sensor 60e interacts with oil that is urged by the pump 220, such as to return to the cooking appliance 1, or to another vessel such a different cooking appliance or a vessel (not shown) for storage.

The sensor 60 may be configured to measure the parameter of the oil as oil flows past the sensor as urged by the pump 220 or as urged by gravity, and/or when oil is still with respect to the sensor. In the latter case (oil parameter is measured when the oil is still), the sensor 60b may be provided and the first valve 40 may be aligned such that the valve is ported for fluid communication between the first and third ports 41, 43, with the second port being closed. This alignment of the second valve in combination with the pump 220 being secured causes a slug of oil within the pipe 18 to remain still. In some embodiments, the second valve 40a, when provided, may also be aligned to prevent flow through the first port 41a.

In some embodiments, the sensor 60 may provide a signal to the display 999 that is indicative of the measured electrical property of the oil, such that the display 999 can provide a measured value of the oil to the user to allow the user to take action, such as by adjusting the position of a valve 140 (140a), such as to continue filtering the oil through the filter material 180a, such as by aligning the second valve 140a to flow from the first port 141a to the third port 143a to return to the vat 180b to pass through the filter an additional time.

While the preferred embodiments of the disclosed have been described, it should be understood that the invention is not so limited and modifications may be made without departing from the disclosure. The scope of the disclosure is defined by the appended claims, and all devices that come within the meaning of the claims, either literally or by equivalence, are intended to be embraced therein.

The invention claimed is:

1. A system for measuring the state of degradation of cooking oil comprising:
a vat for receipt of cooking oil, the vat remote from a device used to cook food product with cooking oil;
a pump in fluid communication with the vat, the pump fluidly connected to take suction from the vat;
a sensor disposed in fluid communication within the vat and adapted to measure an electrical property that is indicative of the quality of the cooking oil within the vat;
wherein the sensor is disposed in a fluid conduit that is in fluid communication with the pump, further comprising a vent line disposed in fluid communication with the fluid conduit proximate to the sensor, the vent line in communication with the vat,
wherein the vent line has an inner diameter that is smaller than an inner diameter of the fluid conduit.

2. The system of claim 1, wherein the vat comprises a filtering media disposed therein the filtering media configured to remove impurities from cooking oil that flows through the filtering media.

3. The system of claim 2, wherein the vent line is disposed between the filtering media and the pump.

4. The system of claim 1, wherein the inner diameter of the vent line is at least three times smaller than the inner diameter of the fluid conduit.

5. The system of claim 1, wherein the vent line is disposed between the sensor and a first isolation valve, the first isolation valve being adjustable between a first position to allow fluid flow therethrough and a second position to prevent fluid flow therethrough.

6. The system of claim 5, further comprising a second isolation valve that is disposed on an opposite side of the sensor as the vent line.

7. The system of claim 5, further comprising a second valve that is disposed in the vent line.

8. The system of claim 7, further comprising a controller that controls the position of each of the first isolation valve and the second valve and maintains the positions of the first isolation valve and the second valve in an opposite position to each other.

9. The system of claim 7, wherein the second isolation valve receives a signal from the first valve that is indicative of the position of the first valve, wherein the second isolation valve is configured to be automatically positioned into a position that is opposite the position of the first valve with a master/slave relationship.

10. The system of claim 1, wherein the vent line is disposed downstream of a discharge side of the pump.

11. The system of claim 1, wherein the sensor is configured to measure an electrical property that is indicative of the total polar materials of the cooking oil.

12. The system of claim 1, wherein the sensor is configured to measure the electrical property of the cooking oil when the cooking oil flows past the sensor.

13. A system for measuring the state of degradation of cooking oil in a deep fryer comprising:
at least one fryer pot;
a loop of piping fluidly connected to said at least one fryer pot for selectively allowing flow of oil from the at least one fryer pot into the loop and for selectively allowing the cooking oil to return to said at least one fryer pot from the loop;
a pump for urging the flow of cooking oil through the loop of piping and selectively to urge oil to return to the at least one fryer pot,
the loop further comprising a first valve that is positionable to a closed position to prevent oil flow to or from the at least one fryer pot, and is positioned to an open position to allow flow to or from the at least one fryer pot,
the loop further comprises a return portion that extends from a discharge of the pump toward a suction of the pump, wherein the return portion includes a second valve that is configured to selectively prevent or allow flow through the return portion;
a sensor disposed in fluid communication within the loop and adapted to measure an electrical property that is indicative of the quality of the cooking oil within the loop of piping, wherein the sensor is disposed in the return portion of the loop,
wherein the return portion of the loop further comprises a vent line disposed proximate to the sensor, wherein fluid within the loop can flow into and through the vent line,
further comprising a controller that receives a signal from the sensor indicative of the measured electrical property of the oil, wherein the first and second valves are remotely operable by the controller, and the controller is configured to selectively operate one or both of the first and second valves based upon the measured electrical property of the oil, wherein the vent line further comprises a third valve disposed therein, wherein the third valve is remotely operated by the controller to a closed position when the second valve is open, and the third valve is remotely operated to the open position when the second valve is closed.

14. The system of claim 13, wherein the diameter of the vent line is at least 3 times smaller than a diameter of the return portion of the loop.

15. The system of claim 13, wherein the sensor is configured to measure the electrical property of the cooking oil when the cooking oil flows past the sensor.

16. The system of claim 13, further comprising an oil filtration system that is disposed in fluid communication with the loop.

17. The system of claim 16, wherein the vent line drains into the oil filtration system.

18. The system of claim 13 further comprising a fourth valve positioned within the return portion and located between the sensor and an oil filtration system, such that oil flowing through the return portion flows first through the sensor, then through the third valve, and then into the oil filtration system.

19. The system of claim 13,
further comprising a fourth valve positioned within the return potion and located between the sensor and an oil filtration system such that oil flowing through the return portion flows first through the sensor, then through the fourth valve, and then into the oil filtration system, wherein the controller maintains the position of the third valve in the opposite position as the fourth valve.

20. A system for measuring the state of degradation of cooking oil in a deep fryer comprising:
at least one fryer pot;
a loop of piping fluidly connected to said at least one fryer pot for selectively allowing flow of oil from the at least one fryer pot into the loop and for selectively allowing the cooking oil to return to said at least one fryer pot from the loop;
a pump for urging the flow of cooking oil through the loop of piping and selectively to urge oil to return to the at least one fryer pot,
the loop further comprises a recirculation portion that extends from a discharge of the pump toward a suction of the pump, wherein the recirculation portion includes a first valve that is configured to selectively prevent or allow flow through the recirculation portion;
a sensor disposed in fluid communication within the loop and adapted to measure an electrical property that is indicative of the quality of the cooking oil within the loop of piping, wherein the sensor is disposed in the recirculation portion of the loop,
further comprising a vent line positioned within the recirculation portion and proximate to the sensor, wherein the vent line comprises a second valve disposed therein, and further comprising a controller that is in communication to operate the first and second valves, wherein the controller maintains the first and second valves in the opposite positions to each other.

21. The system of claim 20, further comprising a third valve that is disposed within the loop of piping and proximate to a drain of the at least one fryer pot and a fourth valve that is disposed within the loop of piping and proximate to a return of the at least one fryer pot.

22. The system of claim 21, wherein the third and fourth valves are shut during operation of the sensor.

23. The system of claim 21, wherein the third and fourth valves are open during operation of the sensor.

24. A system for measuring the state of degradation of cooking oil in a deep fryer comprising:
at least one fryer pot;
a loop of piping fluidly connected to said at least one fryer pot for selectively allowing flow of oil from the at least one fryer pot into the loop and for selectively allowing the cooking oil to return to said at least one fryer pot from the loop;
a pump for urging the flow of cooking oil through the loop of piping and selectively to urge oil to return to the at least one fryer pot,
the loop further comprises a recirculation portion that extends from a discharge of the pump toward a suction of the pump, wherein the recirculation portion includes a first valve that is configured to selectively prevent or allow flow through the recirculation portion;
a sensor disposed in fluid communication within the loop and adapted to measure an electrical property that is indicative of the quality of the cooking oil within the loop of piping, wherein the sensor is disposed in the recirculation portion of the loop, further comprising a vent line positioned within the recirculation portion and proximate to the sensor wherein the vent line comprises a second valve disposed therein, wherein the second valve receives a signal from the first valve that is indicative of the position of the first valve, wherein the second valve is configured to be automatically positioned into a position that is opposite the position of the first valve with a master/slave relationship.

* * * * *